United States Patent
Liu et al.

(10) Patent No.: US 9,969,703 B2
(45) Date of Patent: May 15, 2018

(54) TRIAZINE-CONTAINING PHOTOCURABLE RESIN AND PREPARATION METHOD THEREOF

(71) Applicant: Jiangnan University, Wuxi (CN)

(72) Inventors: Ren Liu, Wuxi (CN); Xiaopeng Zhang, Wuxi (CN); Zhiquan Li, Wuxi (CN); Jingcheng Liu, Wuxi (CN); Jing Luo, Wuxi (CN); Xiaoya Liu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days. days.

(21) Appl. No.: 15/551,594

(22) PCT Filed: Jan. 20, 2016

(86) PCT No.: PCT/CN2016/071435
§ 371 (c)(1),
(2) Date: Aug. 16, 2017

(87) PCT Pub. No.: WO2017/117826
PCT Pub. Date: Jul. 13, 2017

(65) Prior Publication Data
US 2018/0044301 A1    Feb. 15, 2018

(30) Foreign Application Priority Data
Jan. 5, 2016  (CN) ...................... 2016 1 0010125 A

(51) Int. Cl.
C07D 251/70    (2006.01)
C09D 167/06    (2006.01)
C08F 22/22     (2006.01)

(52) U.S. Cl.
CPC ............ C07D 251/70 (2013.01); C08F 22/22 (2013.01); C09D 167/06 (2013.01)

(58) Field of Classification Search
CPC ...... C07D 251/70; C09D 167/06; C08F 22/22
USPC .......................................... 544/196; 524/100
See application file for complete search history.

(56) References Cited

FOREIGN PATENT DOCUMENTS

| CN | 102516326 A | 6/2012 |
|---|---|---|
| CN | 104017128 A | 9/2014 |
| CN | 104650341 A | 5/2015 |

*Primary Examiner* — Venkataram Balasubramanian
(74) *Attorney, Agent, or Firm* — Gokalp Bayramoglu

(57) ABSTRACT

The present invention discloses a triazine-containing photocurable resin and a preparation method thereof. The preparation method of the resin comprises the following steps of: (1) Dissolving the hexamethylolmelamine the unsaturated fatty acids and a catalyst in a solvent, keeping a reaction going, separating and extracting the reaction product after the reaction ends, obtaining triazine-containing fatty acid ester; (2) adding 50 wt % hydrogen peroxide, a catalyst and a solvent, namely methylbenzene, into the triazine-containing fatty acid ester prepared in step (1), keeping a reaction going, obtaining triazine-containing fatty acid ester epoxy resin; (3) adding a polymerization inhibitor and a catalyst into acrylic acid, dropping the triazine-containing fatty acid ester epoxy resin prepared in step (2), keeping a reaction going, and obtaining the triazine-containing photocurable resin. The photocurable resin of the present invention contains a rigid triazine and flexible fatty chains at the same time, so the cured object has excellent comprehensive performance and can be used as the photocurable resin in the field of photosensitive macromolecular materials.

8 Claims, 2 Drawing Sheets

TRIAZINE-CONTAINING PHOTOCURABLE RESIN AND PREPARATION METHOD THEREOF

FIELD OF THE INVENTION

The present invention relates to the technical field of polymer materials, in particular to a method for preparing a triazine-containing photocurable resin that takes a triazine as a center structure by extending unsaturated fatty acid chains and then importing photosensitive groups.

BACKGROUND OF THE INVENTION

Ultraviolet curing technology as an environmentally-friendly, energy-saving and efficient green technology can be used in combination with new materials and new energy sources. photocurable resins based on regenerative resources can be used as one of the optimal solutions for solving problems such as exhaustion of petroleum resources and high environmental requirements that challenge the industrial development.

TECHNICAL PROBLEMS

Plant oil-based acrylate is a widely researched photocurable resin that belongs to regenerative resources, with advantages of low price and high photosensitivity. Meanwhile, due to long fatty chains in the molecular structure, the plant oil-based acrylate is usually with a low resin strength and low modulus, low glass transition temperature, poor adhesion, etc. Introducing rigid kernels to the molecular structure to reduce volume shrinkage and to strengthen the mechanical performance of material has an important significance for preparation of a plant oil-based photocurable resin with high performance.

TECHNICAL SOLUTIONS

Aiming at the aforementioned problems in prior art, the applicant provides a triazine-containing photocurable resin and a preparation method thereof. The photocurable resin of the present invention contains a rigid triazine and flexible fatty chains at the same time, so the cured object has excellent comprehensive performance and can be used as the photocurable resin in the field of photosensitive macromolecular materials.

The technical solution of the present invention is as follows:

A triazine-containing photocurable resin is provided, wherein the preparation method of the resin includes the following steps:

(1) Dissolving hexamethylolmelamine, unsaturated fatty acids and a catalyst in a solvent, stirring the materials at room temperature, heating the materials, keeping a reflux reaction going for 20-48 h, separating and extracting the reaction products after the reaction ends, and then obtaining triazine-containing fatty acids ester;

(2) adding 50 wt % hydrogen peroxide, a catalyst and a solvent methylbenzene into the triazine-containing fatty acids ester which are prepared in step (1), controlling the reaction temperature to be 50-70° C., keeping a reaction going for 6-12 h while stirring the materials, keeping the reaction product still for layering after the reaction ends, removing a water layer after layering, collecting an organic layer, washing the organic layer using the saturated aqueous solution of sodium bicarbonate and de-ionized water until the organic layer becomes neutral, decompressing and distilling the product to remove the solvent, and then obtaining triazine-containing fatty acid ester epoxy resin;

(3) adding a polymerization inhibitor and a catalyst into acrylic acid, heating the mixed materials to 85-105° C., dropping the triazine-containing fatty acid ester epoxy resin prepared in step (2), keeping a reaction going for 4-8 h after the dropping is completed, and then obtaining the triazine-containing photocurable resin.

In step (1), the unsaturated fatty acids are selected from one or more of oleinic acid, linoleic acid, a-linolenic acid, arachidonic acid, petroselinic acid, eleostearic acid, calendula acid, erucic acid and palmitoleic acid; and the molar ratio of the hexamethylolmelamine to the unsaturated fatty acids is 1:6.0-12.0.

In step (1), the catalyst is selected from one or more of dicyclohexylcarbodiimide, 4-dimethylamino-pyridine, 1-(3-dimethylaminopropyl)-3-ethylcarbodiimide hydrochloride, 4-dimethylamino-pyridine, sulfuric acid, benzenesulfonic acid, p-methylbenzene sulfonic acid and styrene sulfonic acid; and the solvent is selected from one of dichloromethane, trichloromethane and methylbenzene.

In step (2), the catalyst is selected from one or more of formic acid, acetic acid and propanoic acid; and the molar ratio of the trizine ring-contained fatty acids to the hydrogen peroxide to the catalyst is 1:1.4-2.2:0.4-0.7.

In step (3), the catalyst is selected from one or more of chromium 2-ethylhexanoate (III), triphenylphosphine, triethanolamine and tetrabutylammonium bromide, in an amount which accounts for 0.5-2.0% of the total mass of the reactants; the polymerization inhibitor is selected from one or more of p-dihydroxybenzene, p-tert-butylhydroquinone and p-methoxyphenolate, in an amount which accounts for 0.10-0.30% of the total mass of the reactants; and the molar ratio of the acrylic acid to the triazine-containing fatty acid ester epoxy resin is 0.8-1.1:1.

The structural formula of the photocurable resin can be seen in formula (1):

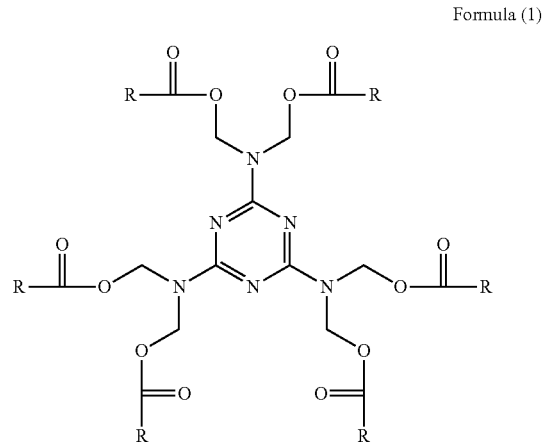

Formula (1)

In the formula (1), R represents

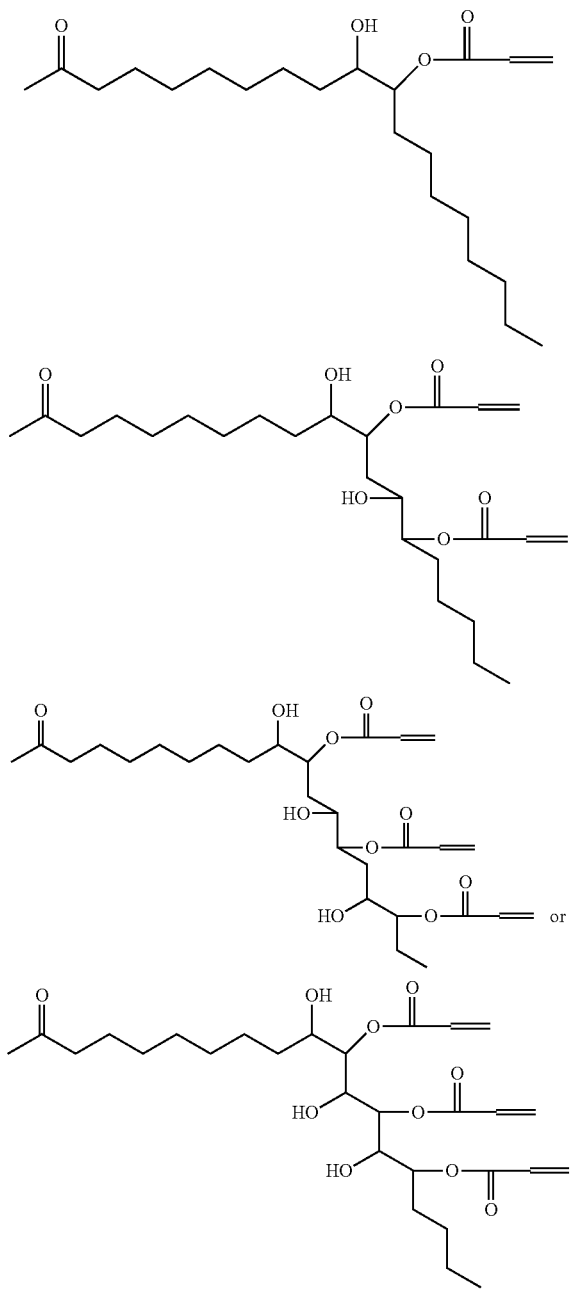

In step (2), the method for preparing the triazine-containing fatty acid ester epoxy resin includes steps of: adding metachloroperbenzoic acid and a solvent into the triazine-containing fatty acids ester prepared in step (1), stirring the mixed materials and keeping a reaction going for 3-24 h at a temperature of 0-30° C., keeping the reaction product still for layering after the reaction ends, collecting the organic layer, washing the organic layer using the saturated aqueous solution of sodium bicarbonate and de-ionized water in turn until the organic layer becomes neutral, decompressing and distilling the organic layer to remove the solvent, and then obtaining the triazine-containing fatty acid ester epoxy resin.

The molar ratio of the metachloroperbenzoic acid to the double bonds in the triazine-containing fatty acid ester is 0.8-2:1, and the solvent is dichloromethane or trichloromethane.

BENEFICIAL EFFECT

The present invention has the following beneficial technical effects:

(1) The photocurable resin of the present invention contains a rigid triazine and flexible fatty chains at the same time, so the cured object has excellent comprehensive performance and can be used as the photocurable resin in the field of photosensitive macromolecular materials.

(2) The photocurable resin of the present invention is the triazine-containing fatty acid ester with a multi-branched structure obtained through the esterification reaction, and the used hexamethylolmelamine and unsaturated fatty acids are both industrial products in low cost.

(3) The epoxy groups are obtained by means of oxidizing double bonds during the preparation of the photocurable resin of the present invention, thus making preparations for importing the acrylic acid.

(4) The fatty acids different in unsaturated degrees are selected to prepare the triazine-containing fatty acid ester epoxy resin with different epoxide numbers, thus finally obtaining the triazine-containing fatty acid ester acrylic resins with different degrees of functionality.

(5) The photocurable resin structure of the present invention contains the triazine structure, so the prepared acrylic resins have relatively high hardness and weather fastness; meanwhile, the resins have good flexibility because of the existence of the fatty acid long carbon chains, and the multi-branch structure can reduce the volume shrinkage after resin curing.

DETAILED DESCRIPTION OF PARTICULAR EMBODIMENTS OF THE INVENTION

The present invention is described in detail below in conjunction with the attached drawings and embodiments.

First Embodiment

Figure 1:
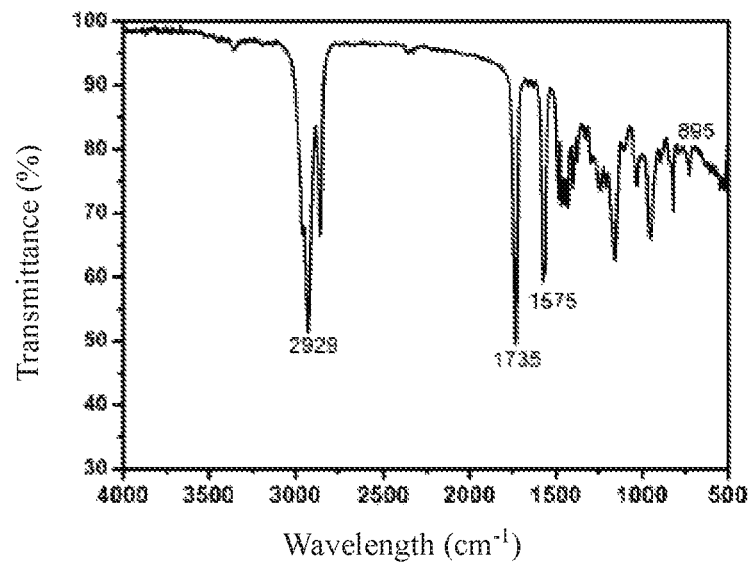
FIG. 1 is an infrared spectrogram of EHMMLO prepared in embodiment 1 of the present invention.
Figure 2:
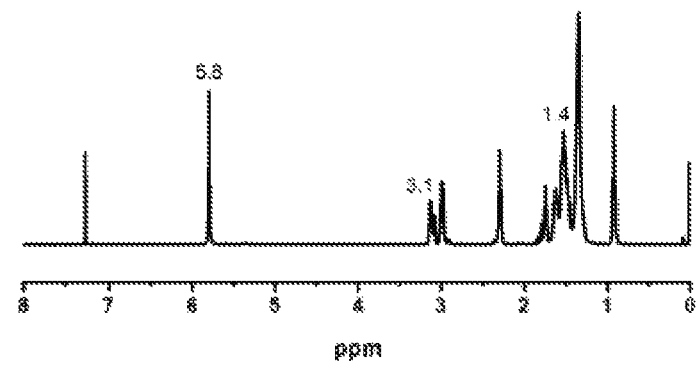
FIG. 2 is a nuclear magnetic resonance spectrogram of the EHMMLO prepared in embodiment 1 of the present invention.
Figure 3:
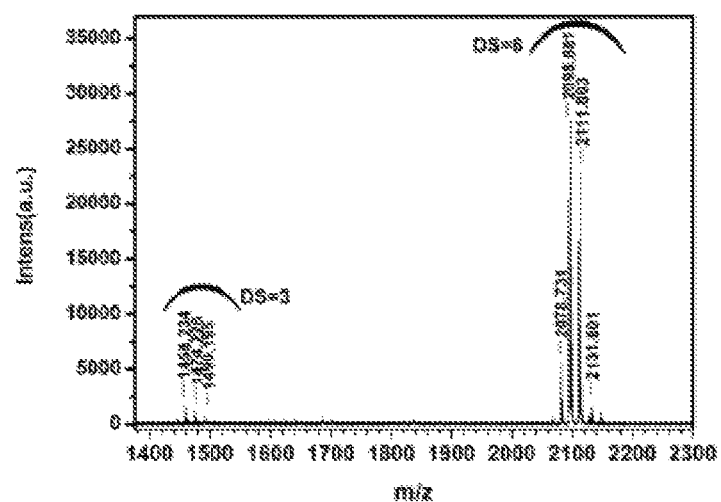
FIG. 3 is a mass spectrum of the EHMMLO prepared in embodiment 1 of the present invention.
Figure 4:
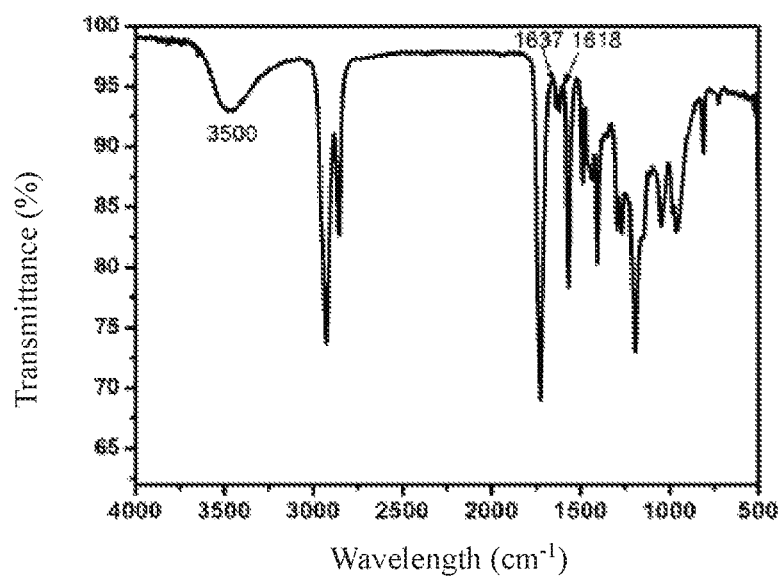
FIG. 4 is an infrared spectrogram of the triazine-containing photocurable resin prepared in embodiment 1.

A triazine-containing photocurable resin is provided. The preparation method of the resin includes the following steps:

(1) 5.00 g of hexamethylolmelamine, 33.86 g of linolenic acid, 24.90 g of dicyclohexylcarbodiimide and 1.48 g of 4-dimethylamino-pyridine are placed into a three-neck flask; 150 ml of dichloromethane is added to dissolve the added materials; the materials react with stirring for 24 h at room temperature; the reaction product is heated while a reflux reaction is kept going for 28 h; after the reaction ends, the reaction product is filtered to remove the generated salts; the filtrate is decompressed and distilled to remove dichloromethane; the distilled product is extracted with ethanol and dried in vacuum at a temperature of 25° C., and then triazine-containing fatty acid ester (HMMLO) is obtained;

(2) 12.0 g of the triazine-containing fatty acid ester prepared in step (1), 1.14 g of acetic acid and 20 g of methylbenzene are placed in a three-neck flask; 11.8 g of 50 wt % hydrogen peroxide is dropped into the three-neck flask; the reaction temperature is controlled to be 60° C. after the dropping is completed; the materials react with stirring for 8 h; the reaction product is kept still for layering after the reaction ends; the separated water layer is removed; an organic layer is collected and washed using the saturated aqueous solution of sodium bicarbonate and de-ionized water until the organic layer becomes neutral; the organic layer is decompressed and distilled to remove the solvent; and then, the triazine-containing fatty acid ester epoxy resin (EHMMLO) is obtained, wherein the infrared spectrogram of the product can be seen in FIG. 1; the nuclear magnetic resonance spectrogram can be seen in FIG. 2; and the mass spectrum of the product can be seen in FIG. 3;

(3) 3.779 g of acrylic acid, 0.04 g of polymerization inhibitor, namely hydroquinone, and 0.27 g of the catalyst, namely chromium 2-ethylhexanoate (III), are placed in a three-neck flask; the materials are heated to 95° C. with stirring; then, 10 g of the triazine-containing fatty acid ester epoxy resin prepared in step (2) is dropped by using a hopper; a reaction is kept going for 8 h after the dropping is completed; and then, the triazine-containing photocurable resin is obtained, wherein the infrared spectrogram of the product can be seen in FIG. 4.

FIG. 1 is an infrared spectrogram of the triazine-containing fatty acid ester epoxy resin (EHMMLO). From FIG. 1 it can be seen that, the —OH absorption peak disappears at a wavelength in a range of 3000-3500 cm−1; the telescoping and vibrating peak of =C—H— disappears at a wavelength near 3010 cm−1, and the characteristic absorption peak of the epoxy group appears at a wavelength near 895 cm−1.

FIG. 2 is a nuclear magnetic resonance spectrogram of the triazine-containing fatty acid ester epoxy resin (EHMMLO). From FIG. 2 it can be seen that, the absorption peak of the double-bond proton with fatty chains disappears at a concentration in a range of 5.2-5.4 ppm, while the absorption peak of the methylene hydrogen proton adjacent to the ester bond appears at the concentration of 5.8 ppm, and the proton peak of the epoxy group appears at the concentration of 1.4 ppm and at the concentration of 3.1 ppm.

FIG. 3 is a mass spectrum of the triazine-containing fatty acid ester epoxy resin (EHMMLO). From the MALDI-TOF characterization it can be seen that, two main peaks exists; the m/z difference of the two peaks is 674-641, which is equivalent to the molecular weight of three linolenic acid molecular chains; each one of the peaks represents a degree of substitution, therefore two degrees of substitution, DS=3 and DS=6, can be determined according to the m/z value.

In accordance with the above characterization, the triazine-containing fatty acid ester epoxy resin is successfully synthesized.

FIG. 4 is an infrared spectrogram of the triazine-containing photocurable resin. From FIG. 4 it can be seen that the —OH absorption peaks at a wavelength near 3500 cm−1; strong telescoping and vibrating peak of —C=C— appears at the wavelength of 1618 cm−1 and at wavelength of 1637 cm−1, which means that the target product is successfully synthesized.

Second Embodiment (1) 7.00 g of hexamethylolmelamine, 47.60 g of oleinic acid, 34.86 g of dicyclohexylcarbodiimide and 2.07 g of 4-dimethylamino-pyridine are placed into a three-neck flask; 250 ml of dichloromethane is added to dissolve the added materials; the materials react with stirring for 24 h at room temperature; the reaction product is heated while a reflux reaction is kept going for 24 h; after the reaction ends, the reaction product is filtered to remove the generated salts; the filtrate is decompressed and distilled to remove dichloromethane; the distilled product is extracted with ethanol and dried in vacuum at a temperature of 25° C., and then triazine-containing fatty acid ester (HMMLO) is obtained;

(2) 15.0 g of the triazine-containing fatty acid ester prepared in step (1), 1.11 g of formic acid and 30 g of methylbenzene are placed in a three-neck flask; 14.8 g of 50 wt % hydrogen peroxide is dropped into the three-neck flask; the reaction temperature is controlled to be 60° C. after the dropping is completed; the materials react with stirring for 8 h; the reaction product is kept still for layering after the reaction ends; the separated water layer is removed; an organic layer is collected and washed using the saturated aqueous solution of sodium bicarbonate and de-ionized water until the organic layer becomes neutral; the organic layer is decompressed and distilled to remove the solvent; and then, the triazine-containing fatty acid ester epoxy resin (EHMMLO) is obtained;

(3) 3.25 g of acrylic acid, 0.04 g of polymerization inhibitor, namely p-methoxyphenol, and 0.14 g of the catalyst, namely triphenylphosphine, are placed in a three-neck flask; the materials are heated to 105° C. with stirring; then, 10 g of the triazine-containing fatty acid ester epoxy resin prepared in step (2) is dropped by using a hopper; a reaction is kept going for 8 h after the dropping is completed; and then, the triazine-containing photocurable resin is obtained.

Third Embodiment (1) 2.00 g of hexamethylolmelamine, 18.06 g of linolenic acid, 13.28 g of dicyclohexylcarbodiimide and 0.79 g of 4-dimethylamino-pyridine are placed into a three-neck flask; 60 ml of trichloromethane is added to dissolve the added materials; the materials react with stirring for 12 h at room temperature; the reaction product is heated while a reflux reaction is kept going for 12 h; after the reaction ends, the reaction product is filtered to remove the generated salts; the filtrate is decompressed and distilled to remove trichloromethane; the distilled product is extracted with ethanol and dried in vacuum at a temperature of 25° C., and then triazine-containing fatty acid ester (HMMLO) is obtained;

(2) 12.0 g of the triazine-containing fatty acid ester prepared in step (1), 41.8 g of metachloroperbenzoic acid and 300 ml of dichloromethane are placed in a three-neck flask; the mixed materials react with stirring for 10 h at a temperature of 0° C.; the reaction product is kept still for layering after the reaction ends; an organic layer is collected and washed using the saturated aqueous solution of sodium bicarbonate and de-ionized water until the organic layer becomes neutral; the organic layer is decompressed and distilled to remove the solvent; and then, the triazine-containing fatty acid ester epoxy resin (EHMMLO) is obtained;

(3) 3.5 g of acrylic acid, 0.03 g of polymerization inhibitor, namely p-tert-butylhydroquinone, and 0.13 g of the catalyst, namely tetrabutyl ammonium bromide, are placed in a three-neck flask; the materials are heated to 100° C. with stirring; then, 10 g of the triazine-containing fatty acid ester epoxy resin prepared in step (2) is dropped by using a hopper; a reaction is kept going for 8 h after the dropping is completed; and then, the triazine-containing photocurable resin is obtained.

Forth Embodiment (1) 7.50 g of hexamethylolmelamine, 53.3 g of eleostearic acid, 36.6 g of dicyclohexylcarbodiimide and 2.21 g of 4-dimethylamino-pyridine are placed into a three-neck flask; 250 ml of trichloromethane is added to dissolve the added materials; the materials react with stirring for 12 h at room temperature; the reaction product is heated while a reflux reaction is kept going for 12 h; after the reaction ends, the reaction product is filtered to remove the generated salts; the filtrate is decompressed and distilled to remove trichloromethane; the distilled product is extracted with ethanol and dried in vacuum at a temperature of 25° C., and then triazine-containing fatty acid ester (HMMLO) is obtained;

(2) 12.0 g of the triazine-containing fatty acid ester prepared in step (1), 33.9 g of metachloroperbenzoic acid and 250 ml of dichloromethane are placed in a three-neck flask; the mixed materials react with stirring for 8 h at a temperature of 0° C.; the reaction product is kept still for layering after the reaction ends; an organic layer is collected and washed using the saturated aqueous solution of sodium bicarbonate and de-ionized water until the organic layer becomes neutral; the organic layer is decompressed and distilled to remove the solvent; and then, the triazine-containing fatty acid ester epoxy resin (EHMMLO) is obtained;

(3) 2.8 g of acrylic acid, 0.03 g of polymerization inhibitor, namely p-tert-butylhydroquinone, and 0.13 g of the catalyst, namely tetrabutyl ammonium bromide, are placed in a three-neck flask; the materials are heated to 105° C. with stirring; then, 10 g of the triazine-containing fatty acid ester epoxy resin prepared in step (2) is dropped by using a hopper; a reaction is kept going for 8 h after the dropping is completed; and then, the triazine-containing photocurable resin is obtained.

Fifth Embodiment (1) 7.50 g of hexamethylolmelamine, 56.30 g of palmitoleic acid, 36.6 g of dicyclohexylcarbodiimide and 2.21 g of 4-dimethylamino-pyridine are placed into a three-neck flask; 250 ml of trichloromethane is added to dissolve the added materials; the materials react with stirring for 24 h at room temperature; the reaction product is heated while a reflux reaction is kept going for 24 h; after the reaction ends, the reaction product is filtered to remove the generated salts; the filtrate is decompressed and distilled to remove trichloromethane; the distilled product is extracted with ethanol and dried in vacuum at a temperature of 25° C., and then triazine-containing fatty acid ester (HMMLO) is obtained;

(2) 15.0 g of the triazine-containing fatty acid ester prepared in step (1), 1.49 g of formic acid and 30 g of methylbenzene are placed in a three-neck flask; 16.8 g of 50 wt % hydrogen peroxide is dropped into the three-neck flask; the reaction temperature is controlled to be 60° C. after the dropping is completed; the materials react with stirring for 8 h; the reaction product is kept still for layering after the reaction ends; the separated water layer is removed; an organic layer is collected and washed using the saturated aqueous solution of sodium bicarbonate and de-onized water until the organic layer becomes neutral; the organic layer is decompressed and distilled to remove the solvent; and then, the triazine-containing fatty acid ester epoxy resin (EHMMLO) is sobtained;

(3) 2.9 g of acrylic acid, 0.03 g of polymerization inhibitor, namely p-dihydroxybenzene, and 0.13 g of the catalyst, namely triethanolamine, are placed in a three-neck flask; the materials are heated to 9° C. with stirring; then, 10 g of the triazine-containing fatty acid ester epoxy resin prepared in step (2) is dropped by using a hopper; a reaction is kept going for 8 h after the dropping is completed; and then, the triazine-containing photocurable resin is obtained.

What is claimed is:

1. A preparation method of a triazine containing photocurable resin, comprising the following steps:
   (1) dissolving a hexamethylolmelamine, an unsaturated fatty acid and a first catalyst in a first solvent to obtain a first solution, stirring the first solution at room temperature, heating the first solution refluxing for 20-48 h to form a plurality of first reaction products, separating and extracting the plurality of first reaction products to obtain a triazine-containing fatty acids ester;
   (2) adding 50 wt % hydrogen peroxide, a second catalyst and a second solvent of methylbenzene into the triazine-containing fatty acids ester prepared in step (1) to obtain a second solution, stirring the second solution for 6-12 h at a temperature of 50-70° C. to obtain a second product, keeping the second reaction product still for layering, removing a water layer after layering, collecting an organic layer, washing the organic layer with a saturated aqueous solution of sodium bicarbonate and a de-ionized water until the organic layer is neutral, decompressing and distilling the neutral organic layer to remove the second solvent to obtain a triazine-containing fatty acid ester epoxy resin;
   (3) adding a polymerization inhibitor and a third catalyst into an acrylic acid to obtain a mixed material, heating the mixed material to 85-105° C., dropping the triazine-containing fatty acid ester epoxy resin prepared in step (2) into the mixed material, keeping the mixed material at 80-105° C. for 4-8 h after the dropping is completed to obtain a triazine-containing photocurable resin.

2. The preparation method according to claim 1, wherein in step (1), the unsaturated fatty acid is one or more selected from a group consisting of oleinic acid, linoleic acid, linolenic acid, arachidonic acid, petroselinic acid, eleostearic acid, calendula acid, erucic acid and palmitoleic acid; and a molar ratio of the hexamethylolmelamine to the unsaturated fatty acids is 1:6.0-12.0.

3. The preparation method according to claim 1, wherein in step (1), the first catalyst is one or more selected from a group consisting of dicyclohexylcarbodiimide, 4-dimethylamino-pyridine, 1-(3-dimethylaminopropyl)-3-ethylcarbodiimide hydrochloride, sulfuric acid, benzenesulfonic acid, p-methylbenzene sulfonic acid and styrene sulfonic acid; and the first solvent is a solvent selected from a group consisting of dichloromethane, trichloromethane and methylbenzene.

4. The preparation method according to claim 1, wherein in step (2), the second catalyst is one or more selected from a group consisting of formic acid, acetic acid and propanoic acid; and a molar ratio of the trizine ring-contained fatty acids ester to the hydrogen peroxide to the second catalyst is 1:1.4-2.2:0.4-0.7.

5. The preparation method according to claim 1, wherein in step (3), the third catalyst is one or more selected from a group consisting of chromium 2-ethylhexanoate (III), triphenylphosphine, triethanolamine and tetrabutylammonium bromide, wherein an amount of the third catalyst accounts for 0.5-2.0% of a total mass of a reactants; the polymerization inhibitor is one or more selected from a group consisting of p-dihydroxybenzene, p-tert-butylhydroquinone and p-methoxyphenolate, wherein an amount of the polymerization inhibitor accounts for 0.10-0.30% of the total mass of the reactants; and a molar ratio of the acrylic acid to the triazine-containing fatty acid ester epoxy resin is 0.8-1.1:1.

6. The photocurable resin, wherein the photocurable resin comprising a triazin, wherein the structural formula of the photocurable resin is shown in formula (1):

formula (1)

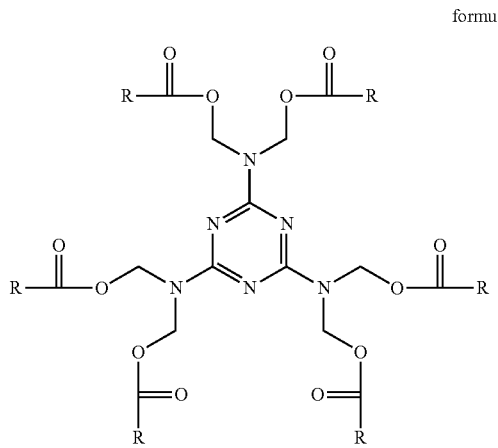

wherein in the formula (1), the R group represents $R_1$, $R_2$, $R_3$ or $R_4$; wherein $R_1$ is:

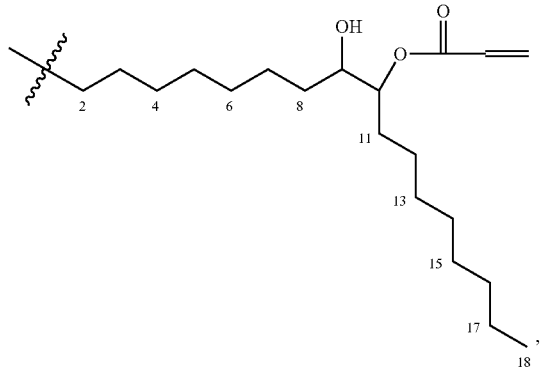 [SMILES: *CCCCCCCC(O)C(CCCCCCCC)OC(=O)C=C]

$R_2$ is:

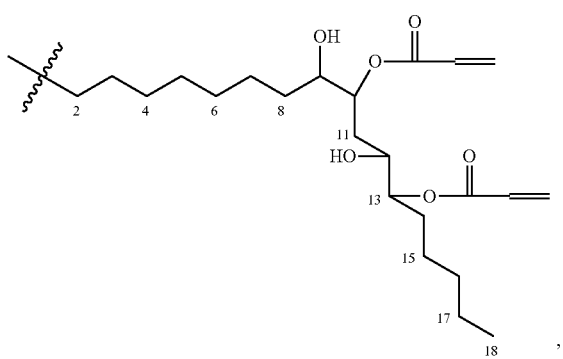 [SMILES: *CCCCCCCC(O)C(CC(O)C(CCCCC)OC(=O)C=C)OC(=O)C=C]

$R_3$ is:

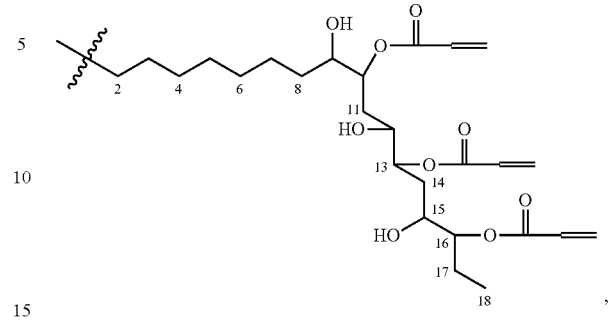

and $R_4$ is:

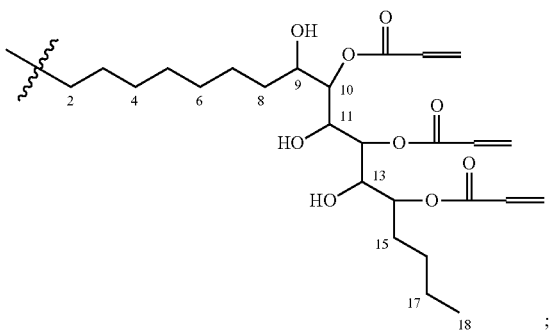 [SMILES: *CCCCCCCC(O)C(OC(=O)C=C)C(O)C(OC(=O)C=C)C(O)C(CCCC)OC(=O)C=C]

wherein the $2^{nd}$ carbon atom of $R_1$, $R_2$, $R_3$, and $R_4$ are linked to the —CO of formula (1).

7. The preparation method according to claim 1, wherein in step (2), the method for preparing the triazine-containing fatty acid ester epoxy resin comprising steps of: adding a metachloroperbenzoic acid and a third solvent into the triazine-containing fatty acids ester prepared in step (1) to obtain a third solution, stirring the third solution for 3-24 h at a temperature of 0-30° C. to obtain a third reaction product, keeping the third reaction product still for layering, collecting the organic layer thereof, washing the organic layer using the saturated aqueous solution of sodium bicarbonate and de-ionized water in turn until the organic layer is neutral, decompressing and distilling the organic layer to remove the third solvent to obtain the triazine-containing fatty acid ester epoxy resin.

8. The preparation method according to claim 7, wherein a molar ratio of the metachloroperbenzoic acid to the triazine-containing fatty acid ester is 0.8-2:1, and the third solvent is dichloromethane or trichloromethane.

* * * * *